(12) United States Patent
Wren

(10) Patent No.: US 9,980,749 B2
(45) Date of Patent: May 29, 2018

(54) ARTIFICIAL INSEMINATION DILDO

(71) Applicant: Dione Arlee Wren, Los Angeles, CA (US)

(72) Inventor: Dione Arlee Wren, Los Angeles, CA (US)

( * ) Notice: Subject to any disclaimer, the term of this patent is extended or adjusted under 35 U.S.C. 154(b) by 226 days.

(21) Appl. No.: 15/189,863

(22) Filed: Jun. 22, 2016

(65) Prior Publication Data

US 2016/0374724 A1 Dec. 29, 2016

Related U.S. Application Data

(60) Provisional application No. 62/183,423, filed on Jun. 23, 2015.

(51) Int. Cl.
*A61B 17/43* (2006.01)
*A61H 19/00* (2006.01)

(52) U.S. Cl.
CPC ............ *A61B 17/43* (2013.01); *A61H 19/44* (2013.01); *A61H 19/50* (2013.01); *A61H 2201/105* (2013.01); *A61H 2201/165* (2013.01)

(58) Field of Classification Search
CPC .... A61B 17/425–17/435; A61H 19/00–19/50; A61D 19/00–19/04; B01L 3/02–3/0296; A61F 2005/411–2005/418
See application file for complete search history.

(56) References Cited

U.S. PATENT DOCUMENTS

| 2011/0224482 | A1* | 9/2011 | McCarthy | A61B 17/43 600/35 |
| 2014/0107410 | A1* | 4/2014 | Rosenberg | A61H 19/44 600/38 |
| 2014/0200400 | A1* | 7/2014 | Berman | A61B 17/43 600/38 |
| 2014/0309488 | A1* | 10/2014 | Fowler | A61B 17/43 600/35 |

* cited by examiner

*Primary Examiner* — Catherine B Kuhlman
(74) *Attorney, Agent, or Firm* — Changi Wu Law Office

(57) ABSTRACT a sexual stimulation and insemination apparatus, comprises a shaft having a tip, a base, and an elongated cylindrical body extending therebetween; a disposable plastic transfer pipette having an open tip, liquid-holding-chamber, and a pipe extending therebetween; a tunnel formed inside the shaft extending from the tip to the base, wherein the tunnel is in a shape of the disposable plastic transfer pipette, and wherein the disposable plastic transfer pipette can be inserted into or removed out of the tunnel; a button, wherein the button is a depressed area formed on the elongated cylindrical body and is located relatively above the liquid-holding-chamber of the disposable plastic transfer pipette when the disposable plastic transfer pipette is inserted in the tunnel; and an O-ring groove formed circumferentially on elongated cylindrical body of the shaft next to the base of said shaft, wherein said O-ring groove is radially smaller than said elongated cylindrical body.

4 Claims, 6 Drawing Sheets

ARTIFICIAL INSEMINATION DILDO

CROSS-REFERENCE RELATED TO RELATED APPLICATIONS

This application claims the benefit and the priority of U.S. Provisional Application No. 62/183,423, filed Jun. 23, 2015, which is hereby incorporated herein by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND

This invention is related to sexual entertainment device and artificial insemination device. For couples wish to conceive, it will need to have a male's sperm in semen to be received by a female's cervix. Normally, the conception can be achieved by an intercourse between a male and a female when the ejaculation of male's penis delivering semen to cervix located behind the vagina. However, for variety of reasons, this cannot be performed normally; therefore, an artificial method to inseminate the cervix will be needed. Furthermore, for sexual excitement purpose, an ejaculation of fluid like lubricants or stimulants during the intercourse may also increase the level of entertainment.

The artificial insemination is normally performed in physician's clinic. The problem of couples having to go to the physician and being inseminated in a sterile, uninviting environment is uncomfortable to most of couples or civil partners. Also, during the intercourse, especially, in the orgasm, the cervix is most open and most susceptible to fertilization. An artificial insemination performed at physician's clinic will not have such environment for orgasmic intercourse, and will be easier to fail. Some options offered now at home are a combination of clamps, tongs, syringes, and turkey basters, or turkey baster-like medical devices that are uncomfortable without the consideration of comfort and inclusion of an emotional, orgasmic experience.

One important issue during insemination is to remain the fluid or semen in a disinfected environment so that there are minimal chances for disease or impurity being transmitted into cervix. At physician's clinic, the medical devices or tools for insemination are mostly made of stainless steel so that they can be sterilized. However, that will be expensive and infeasible for layperson to perform a well disinfection of those insemination tools or the abovementioned options at home.

BRIEF SUMMARY OF THE INVENTION

This Brief Summary is included so as to introduce, in an abbreviated form, various topics to be elaborated upon below in the Detailed Description. This Brief Summary is not intended to identify key or essential aspects of the claimed invention. This brief Summary is similarly not intended for use as an aid in determining the scope of the claims. The subject matters of this application overcomes the aforementioned problems and is directed to a sexual stimulation and insemination apparatus to be used during sexual intercourse that allows one sex partner to fill it with fluid, such as semen, lubricants, or stimulants, and eject the fluid into the other sex partner's cervix. When the fluid is semen, the invention solves the aforementioned problem. When the fluid is other than semen, it can also serve the increase of sexual excitement. The invention, a sexual stimulation and insemination apparatus, comprises a shaft having a tip, a base, and an elongated cylindrical body extending therebetween; a disposable plastic transfer pipette having an open tip, liquid-holding-chamber, and a pipe extending therebetween; a tunnel formed inside the shaft extending from the tip to the base, wherein the tunnel is in a shape of the disposable plastic transfer pipette, and wherein the disposable plastic transfer pipette can be inserted into or removed out of the tunnel; a button, wherein the button is a depressed area formed on the elongated cylindrical body and is located relatively above the liquid-holding-chamber of the disposable plastic transfer pipette when the disposable plastic transfer pipette is inserted in the tunnel; and an O-ring groove formed circumferentially on elongated cylindrical body of the shaft next to the base of said shaft, wherein said O-ring groove is radially smaller than said elongated cylindrical body.

The disposable plastic transfer pipette is normally available in sterilized package at most drugstores. Such disinfected environment is important to prevent any unwanted impurity, bacteria, or virus to be transmitted into cervix during the ejection of the fluid. Also, the entire disposal of the disposable plastic transfer pipette after use can prevent mold or spoilage of semen left inside the disposable plastic transfer pipette. The O-ring groove enables the sexual stimulation and insemination apparatus to be worn by partners or couples on standard dildo wearing devices, such as strap or harness, which will greatly simulate an intercourse and assist the development of sexual pleasure and orgasmic environment.

BRIEF DESCRIPTION OF THE DRAWINGS

It should be understood that the drawings are merely representative, are not necessarily drawn to scale, and are not intended to limit the subject matter of this application.

DETAILED DESCRIPTION

Figure 1:
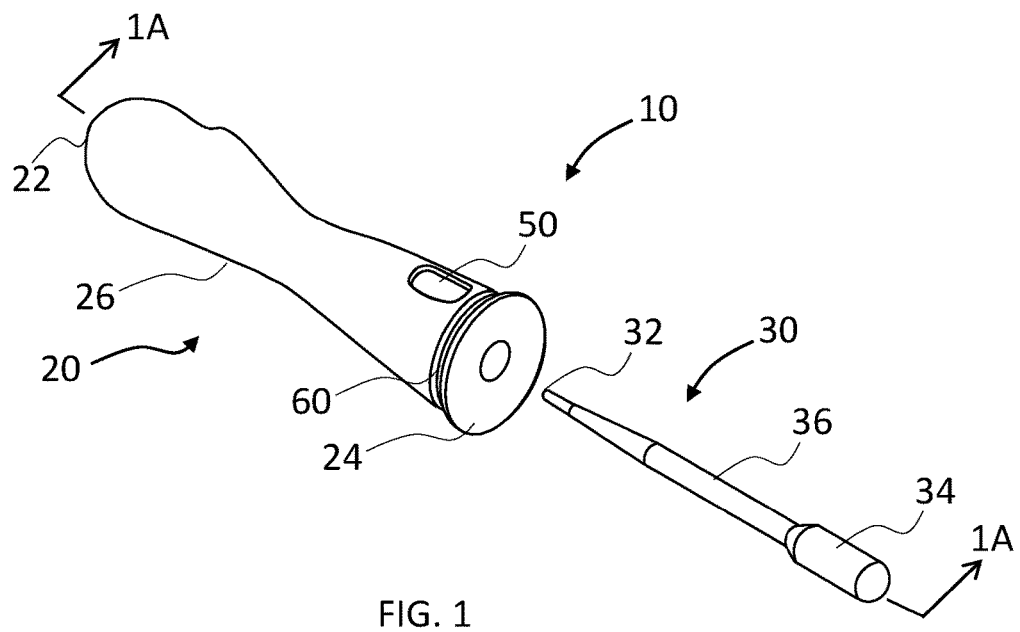
FIG. 1 is a perspective view of one embodiment of the sexual stimulation and insemination apparatus when the disposable plastic transfer pipette is outside the tunnel.

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Other than in the embodiment or example, or where indicated otherwise, all numbers indicating ingredient quantities and/or reaction conditions are to be understood as being modified in every instance by the word "about," which means the ingredient quantities or reaction conditions are within 10 percent to 15 percent of the indicated value.

Unless defined otherwise, all terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" may also include the plural referents unless the context clearly dictates otherwise.

It is further noted that the claims may be drafted to exclude any element that may be optional. As such, this statement is intended to serve as antecedent basis for use of such exclusive terminology as "solely", "only" and the like in connection with the recitation of claim elements, or the use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Figure 1A:
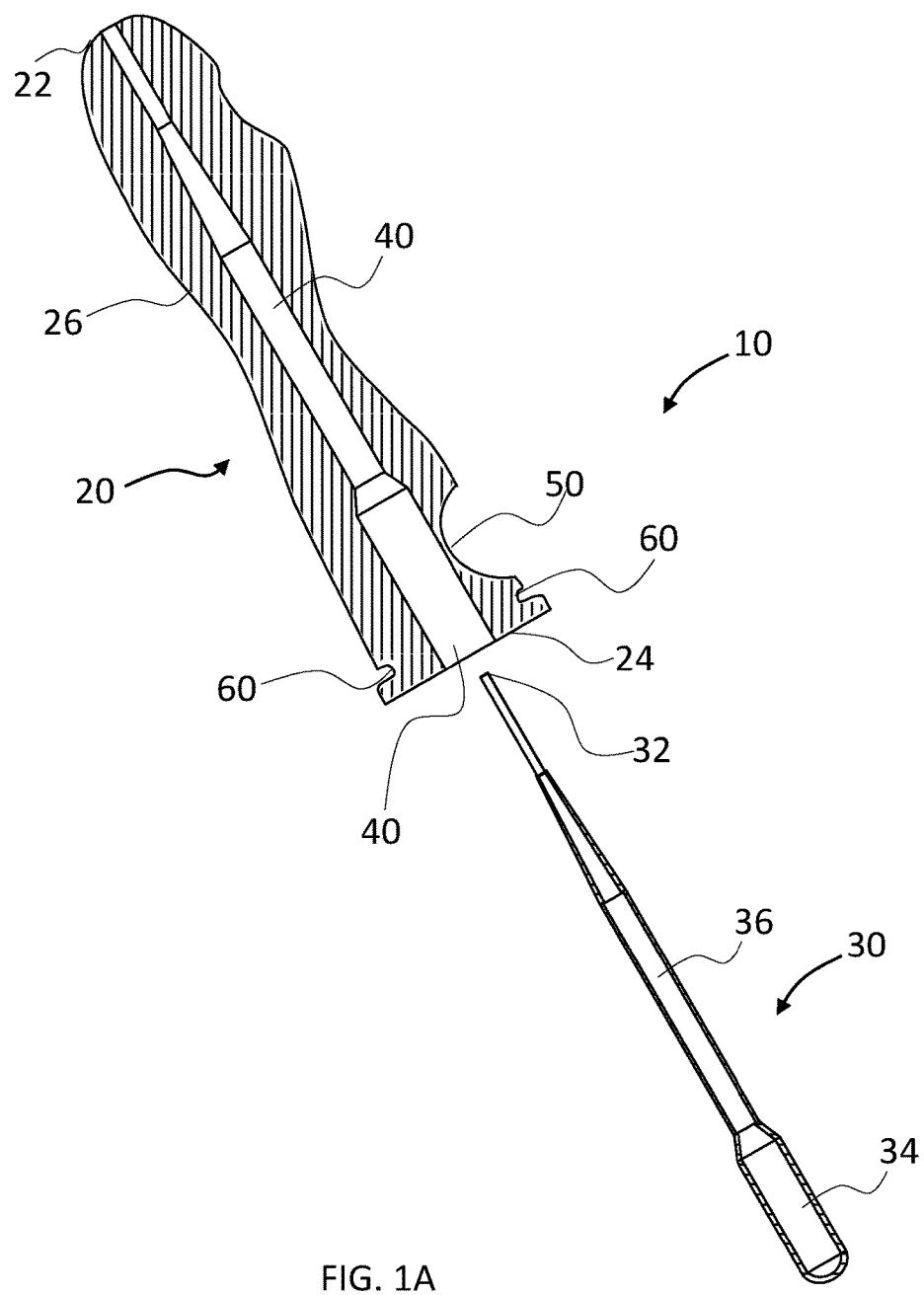
FIG. 1A is a sectional perspective view of one embodiment of the sexual stimulation and insemination apparatus when the disposable plastic transfer pipette is outside the tunnel.
Figure 2:
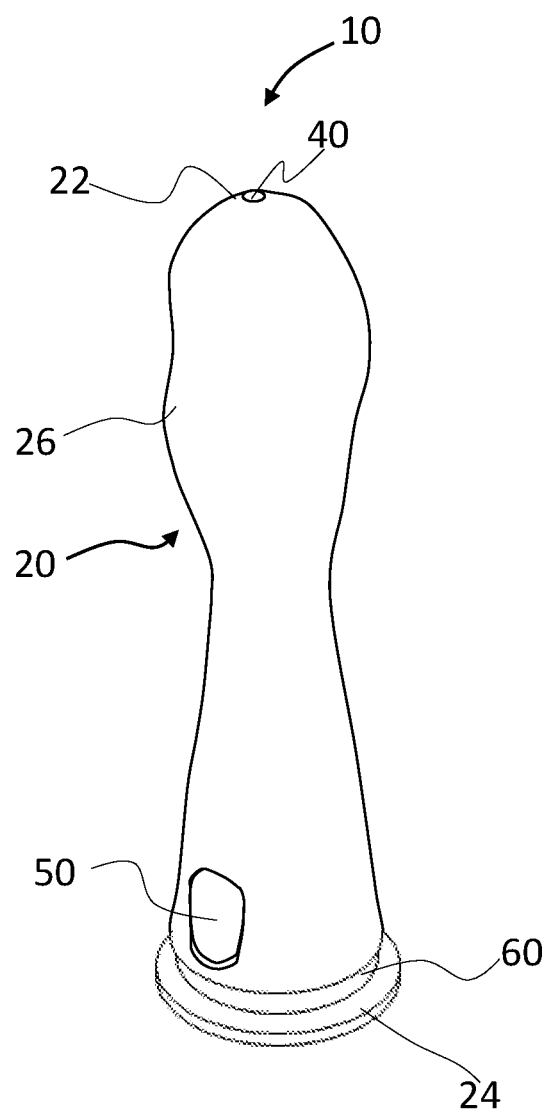
FIG. 2 is a perspective view of one embodiment of the sexual stimulation and insemination apparatus standing on the base of the sexual stimulation and insemination apparatus.

Referring to FIG. 1, FIG. 1A, and FIG. 2, a preferred embodiment of the sexual stimulation and insemination apparatus 10 comprises a shaft 20 having a tip 22, a base 24, and an elongated cylindrical body 26 extending between the tip 22 and the base 24; a disposable plastic transfer pipette 30 having an open tip 32, liquid-holding-chamber 34, and a pipe 36 extending between the open tip 32 and the liquid-holding-chamber 34; a tunnel 40 formed inside the shaft 20 extending from said tip 22 to said base 24, wherein the tunnel 40 is in a shape of the disposable plastic transfer pipette 30, and wherein the disposable plastic transfer pipette 30 can be inserted into or removed out of said tunnel 40; a button 50, wherein button 50 is a depressed area formed on the elongated cylindrical body 26 and is located relatively above the liquid-holding-chamber 34 of the disposable plastic transfer pipette 30 when the disposable plastic transfer pipette 30 is inserted in the tunnel 40; and a O-ring groove 60 formed circumferentially on elongated cylindrical body 26 of said shaft 20 next to said base 24 of said shaft 20, wherein said O-ring groove 60 is radially smaller than said elongated cylindrical body 26. The material of the shaft 20 is made of medical grade, flexible and resilient materials safe to be contacted with mucous membrane, such as silicone, rubber, polyurethane, soft plastic, but preferably silicone. The base 24 is radially larger than the tip 22, so that the sexual stimulation and insemination apparatus 10 can stand vertically on the base 24 (FIG. 2) for better sanitation and easy storage. Note that shaft 20 is in one piece that does not contain any moving parts, connection bolts, or screws, which ensures that no parts will become loose or fall apart to create a health hazard during the use of the sexual stimulation and insemination apparatus 10.

Also referring to FIG. 1 and FIG. 1A, a preferred embodiment of the sexual stimulation and insemination apparatus 10. For increasing the sexual stimulation, the elongated cylindrical body 26 can be curved to have a portion of the elongated cylindrical body 26 to be radially expanded and enlarged.

Figure 3:
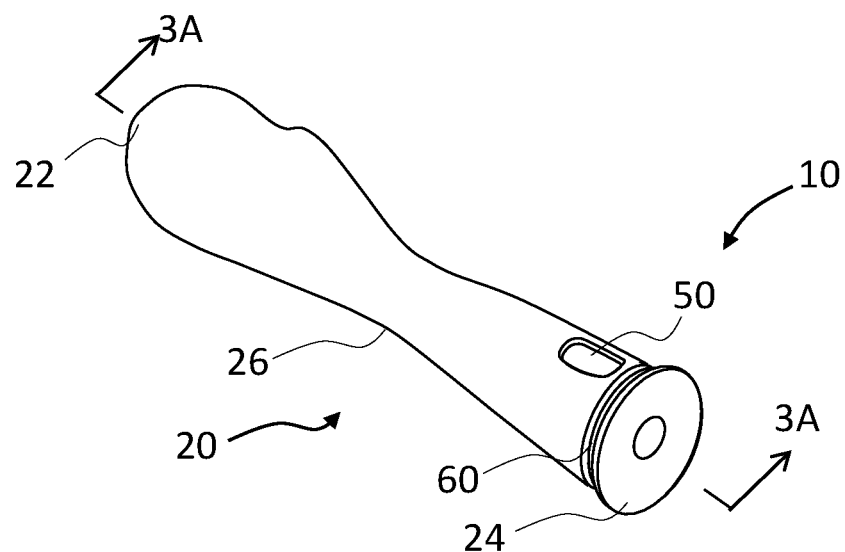
FIG. 3 is a perspective view of one embodiment of the sexual stimulation and insemination apparatus when the disposable plastic transfer pipette is inside the tunnel.
Figure 3A:
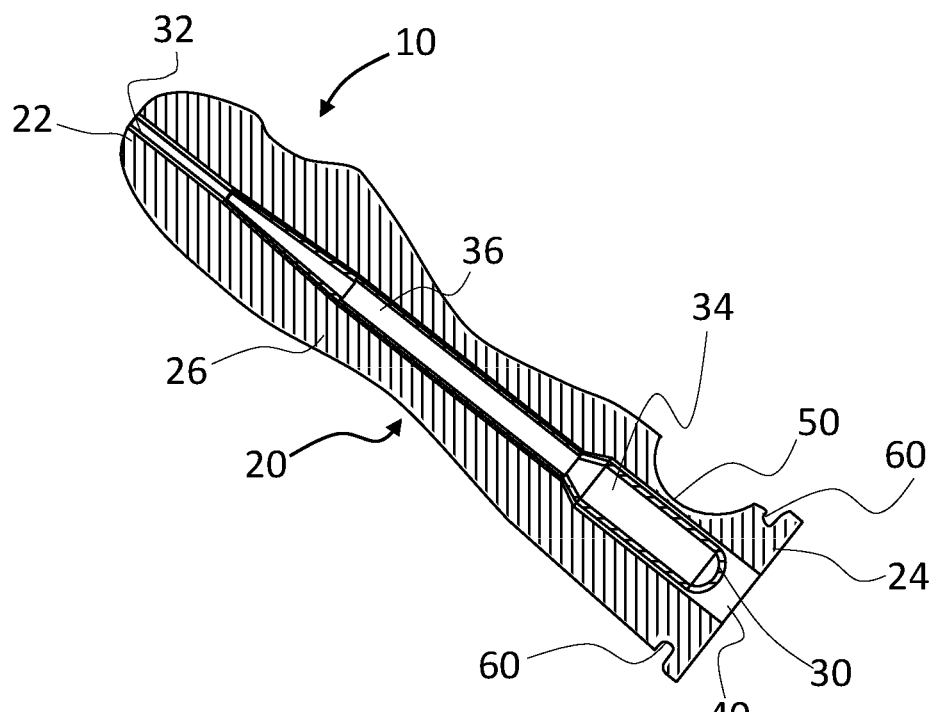
FIG. 3A is a sectional view of one embodiment of the sexual stimulation and insemination apparatus when the disposable plastic transfer pipette is inserted in the tunnel.

Referring to FIG. 3 and FIG. 3A, a preferred embodiment of the sexual stimulation and insemination apparatus 10 is in a position when the disposable plastic transfer pipette 30 is inserted in the tunnel 40. The button 50 is above the liquid-holding-chamber 34. The open tip 32 of the disposable plastic transfer pipette 30 is near the tip 22 of the shaft 20.

Figure 4:
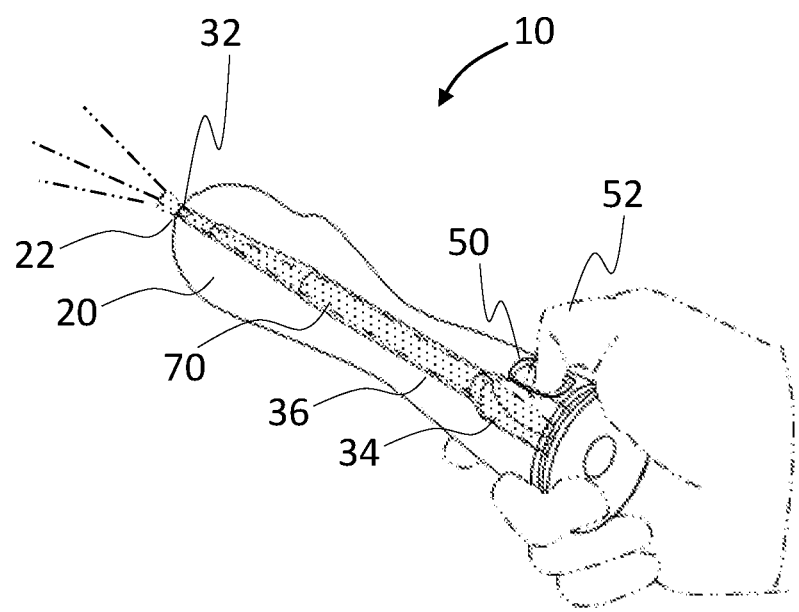
FIG. 4 is a perspective view of one embodiment of the sexual stimulation and insemination apparatus when the button is pressed.

Referring to FIG. 4, a preferred embodiment of the sexual stimulation and insemination apparatus 10 shows that the button 50 is pressed by a human thumb 52. When the button 50 is pressed down by a human thumb 52, the liquid-holding-chamber 34 will be pressurized. Therefore, it causes the fluid 70 contained in the liquid-holding-chamber 34 to be ejected through the pipe 36 and the open tip 32, out of the tip 22, and then into cervix of a female. This action simulates the ejaculation of a penis, which serves one of the purposes of the invention to inseminate a female. The fluid 70 can be semen; however, it can be other fluid, such as water, lubricants, or stimulants in fluid form. After the use of the disposable plastic transfer pipette 30, one can push the tip 22 of the shaft 20 to cause the disposable plastic transfer pipette 30 out of the tunnel 40, and then one can pull out the disposable plastic transfer pipette 30 to discard the used disposable plastic transfer pipette 30. The disposable plastic transfer pipette 30 is normally available in sterilized package at most drugstores. Such disinfection is important to prevent any unwanted impurity, bacteria, or virus to be transmitted into cervix during the ejection of the fluid. Also, the entire disposal of the disposable plastic transfer pipette 30 after use can prevent mold or spoilage of semen left inside the disposable plastic transfer pipette 30 and no semen or fluid to be left in the tunnel 40 or the liquid-holding-chamber 34. Note that the operation to press the button 50 can be performed by a partner during the intercourse or by a single people during self-stimulation and self-insemination.

Figure 5:
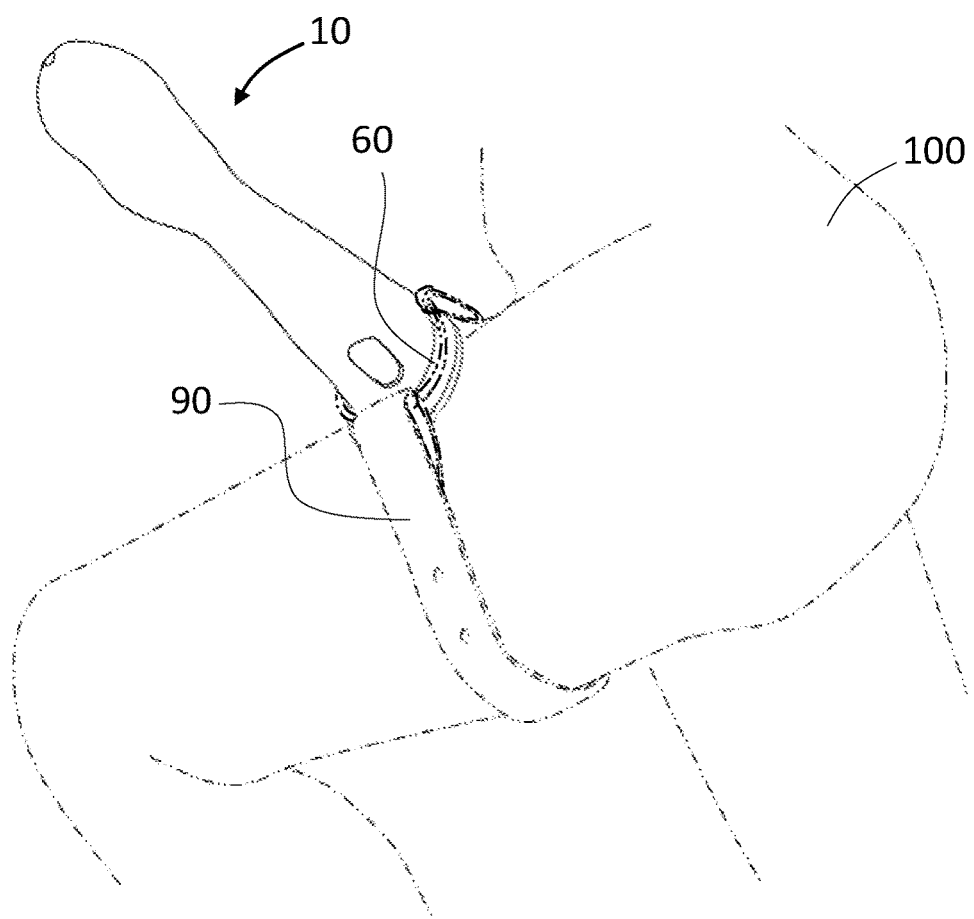
FIG. 5 is a perspective view of one embodiment of the sexual stimulation and insemination apparatus worn by a person.

Referring to FIG. 5, it shows that a preferred embodiment of the sexual stimulation and insemination apparatus 10 can be worn with a standard dildo wearing device 90, such as strap or harness, on the waist, leg, or other preferred body parts of a person 100. By cocking the O-ring groove 60 of the sexual stimulation and insemination apparatus 10 to a standard dildo wearing device 90, the sexual stimulation and insemination apparatus 10 can be worn on a person 100.

In conclusion, the illustrations of the embodiments of a sexual stimulation and insemination apparatus invention that provides an increased sexual pleasure experience and also the function of insemination during such orgasmic environment. Also the disposable and disinfected features of the disposable plastic transfer pipette ensure a hygienic environment during the insemination or sexual enjoyment. Furthermore the design of O-ring groove and base provides versatile ways to use by holding, sitting, or wearing the sexual stimulation and insemination apparatus.

What is claimed:

1. A sexual stimulation and insemination apparatus comprising:
   a shaft having a tip, a base, and an elongated cylindrical body extending therebetween;
   a disposable plastic transfer pipette having an open tip, a liquid-holding-chamber, and a pipe extending therebetween;
   a tunnel formed inside said shaft extending from said tip of said shaft to said base,
   wherein said tunnel is in a shape of said disposable plastic transfer pipette, and
   wherein said disposable plastic transfer pipette can be inserted into or removed out of said tunnel;
   a button, wherein said button is a depressed area formed on the elongated cylindrical body and is located relatively above said liquid-holding-chamber of said disposable plastic transfer pipette when said disposable plastic transfer pipette is inserted in said tunnel; and
   an O-ring groove formed circumferentially on the elongated cylindrical body of said shaft next to said base of said shaft, wherein said O-ring groove is radially smaller than said elongated cylindrical body.

2. The sexual stimulation apparatus of claim 1, wherein said base of said shaft is radially larger than said tip of said shaft.

3. The sexual stimulation and insemination apparatus of claim 1, wherein said shaft is made of medical grade, flexible and resilient materials safe to be contacted with a mucous membrane.

4. A sexual stimulation and insemination apparatus comprising:
   a shaft having a tip, a base, and an elongated cylindrical body extending therebetween, wherein said base of said shaft is radially larger than said tip of said shaft, and wherein said shaft is made of medical grade, flexible and resilient materials safe to be contacted with a mucous membrane;
   a disposable plastic transfer pipette having an open tip, a liquid-holding-chamber, and a pipe extending therebetween;
   a tunnel formed inside said shaft extending from said tip of said shaft to said base, wherein said tunnel is in a shape of said disposable plastic transfer pipette, and wherein said disposable plastic transfer pipette can be inserted into or removed out of said tunnel;
   a button, wherein said button is a depressed area formed on the elongated cylindrical body and is located relatively above said liquid-holding-chamber of said disposable plastic transfer pipette when said disposable plastic transfer pipette is inserted in said tunnel; and
   an O-ring groove formed circumferentially on the elongated cylindrical body of said shaft next to said base of said shaft, wherein said O-ring groove is radially smaller than said elongated cylindrical body.

\* \* \* \* \*